(12) United States Patent
Bolton et al.

(10) Patent No.: US 7,255,880 B2
(45) Date of Patent: Aug. 14, 2007

(54) TREATMENT OF ENDOTHELIN-RELATED DISORDERS

(75) Inventors: Anthony E. Bolton, Bakewell (GB); Arkady Mandel, North York (CA); Duncan J. Stewart, Toronto (CA)

(73) Assignee: Vasogen Ireland Limited, Shannon, County Clare (IE)

( * ) Notice: Subject to any disclaimer, the term of this patent is extended or adjusted under 35 U.S.C. 154(b) by 140 days.

(21) Appl. No.: 10/815,509

(22) Filed: Mar. 31, 2004

(65) Prior Publication Data

US 2004/0253213 A1   Dec. 16, 2004

Related U.S. Application Data

(60) Provisional application No. 60/460,456, filed on Apr. 3, 2003.

(51) Int. Cl.
| | |
|---|---|
| *A61K 35/14* | (2006.01) |
| *A61K 33/00* | (2006.01) |
| *A61K 33/40* | (2006.01) |
| *A61K 47/00* | (2006.01) |
| *A01N 63/00* | (2006.01) |
| *A01N 65/00* | (2006.01) |
| *A01N 59/00* | (2006.01) |
| *A01N 39/00* | (2006.01) |
| *A01N 25/00* | (2006.01) |

(52) U.S. Cl. .................... 424/529; 424/93.7; 424/600; 424/613; 514/771

(58) Field of Classification Search ............... 424/93.7, 424/529, 600, 613; 514/771
See application file for complete search history.

(56) References Cited

U.S. PATENT DOCUMENTS

2002/0051766 A1 *   5/2002   Smith et al. ............... 424/93.7

OTHER PUBLICATIONS

Sakai et al. Pulmonary hypertension caused by congestive heart failure is ameliorated by long-term application of an endothelin receptor antagonist. JACC 1996, 28(6), 1580-1588.*
Cooke et al. Treatment of severe Raynaud's syndrome by injection of autologous blood pretreated by heating, ozonation and exposure to ultraviolet light (H-O-U) therapy. International Angiology 1997, 16(4), 250-254.*
MedlinePlus [online] Medical Encyclopedia: primary pulmonary hypertension [retrieved from the internet] Nov. 12, 2006, http://www.nlm.nih.gov/medlineplus/ency/article/000112.htm Feb. 1, 2005 pp. 1-2.*
S. Babaei, D. J. Stewart, P. Picard, J.C. Monge, "*Effects of VasoCare Therapy on the initiation and progression of aherosclerosis*", Atherosclerosis. 162 (2002) 45-53.

* cited by examiner

*Primary Examiner*—Johann Richter
*Assistant Examiner*—Ernst Arnold
(74) *Attorney, Agent, or Firm*—Foley & Lardner LLP

(57) ABSTRACT

Endothelin-related disorders in mammals can be alleviated by administration to such patients of one or more aliquots of mammalian blood subjected to two or more stressors selected from temperature stressors, electromagnetic emissions and oxidative environments.

19 Claims, 1 Drawing Sheet

TREATMENT OF ENDOTHELIN-RELATED DISORDERS

CROSS-REFERENCE TO RELATED CASES

This application claims the benefit of U.S. Patent Application Ser. No. 60/460,456 filed Apr. 2, 2003, the disclosure of which is incorporated herein by reference.

FIELD OF THE INVENTION

This invention relates to endothelin, and methods for the treatment or prophylaxis of mammalian disorders associated with excessive levels of endothelin.

REFERENCES

1. Babaei, Saeid, et al. "Effects of VasoCare therapy on the initiation and progression of atherosclerosis." Atherosclerosis. 162 (2002) 45-53.

The publication is hereby incorporated by reference in its entirety.

BACKGROUND OF THE INVENTION

Endothelins are a family of 21 amino acid peptides produced by endothelial cells. There are three known isoforms of endothelin, namely endothelin-1 (ET-1), endothelin-2 (ET-2) and endothelin-3 (ET-3). Of the three known isoforms, ET-1 is the major isoform produced by the vascular endothelium and is an extremely potent vasoconstrictor, with veins being 3 to 10 times more sensitive to the effects of ET-1 than arteries.

The vasoconstricting effect of endothelin is caused by the binding of endothelin to its receptor on the vascular smooth muscle cells. Thus far, two endothelin receptors have been characterized in mammalian species, known as the ETA and ETB receptors. The ETA receptor, restricted to vascular smooth muscle, is relatively selective for ET-1 and mediates vasoconstriction. The ETB receptor, primarily located in the endothelium, mediates vasodilatation through the production of endothelium-dependent vasodilators, such as nitric oxide and prostacyclin.

A pathophysiological role for the endothelins has been postulated in a large number of human disease states.

One example of such a disease state is primary pulmonary hypertension (PPH), a rare condition of unknown etiology which affects mainly young people. PPH causes progressive shortening of breath and most of those affected are dead within 4 years of diagnosis. Patients with PPH have increased circulating endothelin levels which may be caused by increased pulmonary endothelin synthesis, and there is evidence to suggest that increased endothelin production may be directly involved in the pathogenesis of PPH (Ferro and Webb, "The Clinical Potential of Endothelin Receptor Antagonists in Cardiovascular Medicine", Drugs 1996 January; 51(1): 12-27).

Another example of such a disease state is glaucoma, which is a group of vascular disorders characterized by degeneration of the optic nerve which carries images from the retina to the brain. The disease is associated with high intraocular pressure and impaired ocular blood flow. There are reports in the literature that ET-1 plasma levels are elevated in some forms of glaucoma (Cellini et al., "Color Doppler imaging and plasma levels of endothelin-1 in low-tension glaucoma": Acta Ophthalmol Scand Suppl 1997; (224): 11-3). Furthermore, endothelin appears to be involved in the regulation of intraocular pressure and the modulation of ocular blood flow (Haefliger et al., "Potential role of nitric oxide and endothelin in the pathogenesis of glaucoma", 1: Surv Ophthalmol 1999 June; 43 Supl 1: S51-8; and Sugiyama et al., "Association of endothelin-1 with normal tension glaucoma: clinical and fundamental studies" 6: Surv Ophthalmol 1995 May; 39 Suppl 1: S49-56), suggesting that endothelin may be involved in the pathogenesis of at least some forms of the disease.

Endothelin also plays a potential role in the progression of atherosclerosis (Rubanyi and Polokoff, "Endothelins: Molecular Biology, Biochemistry, Pharmacology, Physiology and Pathophysiology", Pharmacological Reviews Vol. 46, No. 3, 1994, pp. 325-415) incorporated herein by reference. This is supported by a number of factors, including the following: plasma ET-1 levels are elevated in patients with atherosclerosis and in animal models of hypercholesterolemia; expression of the ET-1 gene is induced, synthesis and release of ET-1 peptide is increased, and binding of exogenous ET-1 is enhanced in the atheromatous vascular lesion; ET-1 production by the endothelium and macrophages is stimulated by oxidized LDL and several cytokines involved in the vascular injury process; and ET-1-induced vasoconstriction is potentiated in atherosclerosis.

Endothelin 1 (ET-1) is also a factor in promotion of angiogenesis, the development of blood vessels, a process which, properly balanced, is important in the restoration and maintenance of good health in mammals. Excess angiogenesis, however, can cause serious health problems, e.g. in recovery from cardiac incidents and in restenosis. ET-1 is known to stimulate the secretion of vascular endothelial growth factor VEGF (see for example Spinella, F. et. al., J. Biol. Chem. 2002 Aug. 2; 277 (31): 27850-5), which promotes angiogenesis. Down-regulation of ET-1 is therefore the basis of potential treatments of conditions involving excess angiogenesis.

Although the symptoms of many endothelin-related disorders can be treated, there is a lack of available treatments which address the underlying role of endothelin in these disorders. Accordingly, the need exists for an effective treatment of endothelin-related disorders.

SUMMARY OF THE INVENTION

It has now been found that levels of endothelin can be reduced in mammalian patients by administration to such patients of one or more aliquots of stressed mammalian blood.

The aliquot of blood is stressed by being subjected to two or more stressors which have been found to modify the blood. According to the invention, the blood aliquot can be modified by subjecting the blood, or separated cellular or non-cellular fractions of the blood, or mixtures of the separated cells and/or non-cellular fractions of the blood, to stressors selected from temperature stressors, electromagnetic emissions and oxidative environments, or any combination of such stressors, simultaneously or sequentially.

Accordingly, in one aspect the present invention provides a method of alleviating the symptoms of an endothelin-related disorder in a mammalian patient suffering therefrom, comprising: (a) treating an aliquot of the patient's blood ex vivo with at least two stressors selected from the group consisting of a temperature above or below body temperature, an electromagnetic emission and an oxidative environment; and (b) administering the aliquot of blood treated in step (a) to the patient.

BRIEF DESCRIPTION OF THE DRAWINGS

The FIGURE of accompanying drawings comprise the following.

DETAILED DESCRIPTION OF PREFERRED EMBODIMENTS

Figure 1:
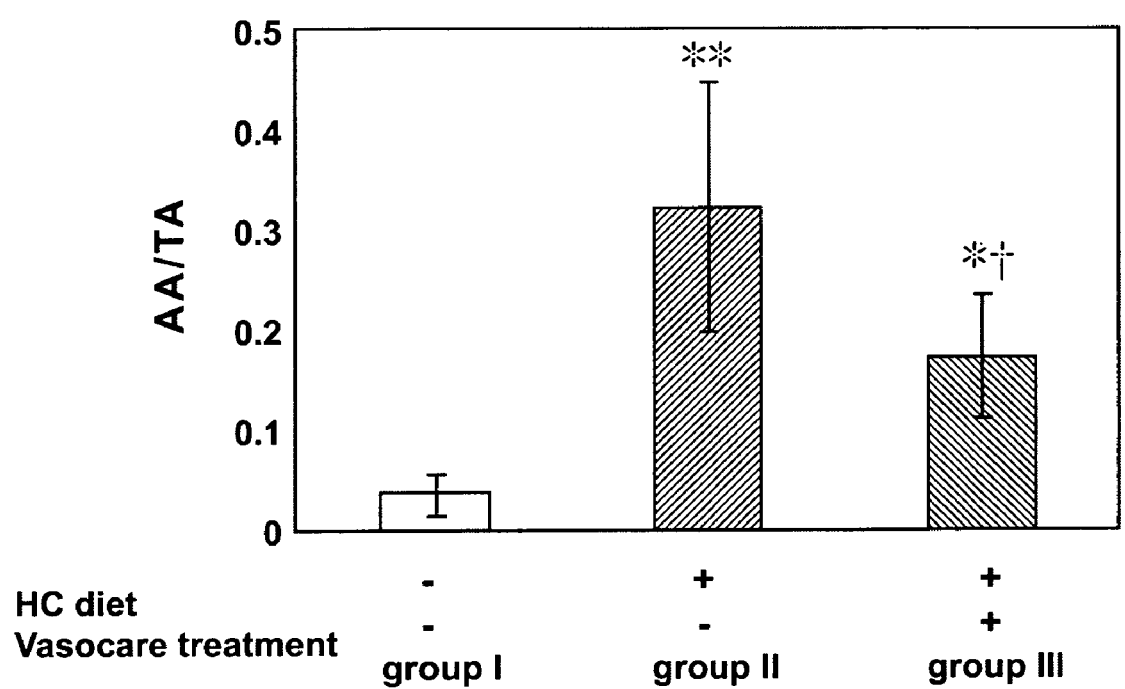
FIG. 1 is a graphical presentation of atherosclerotic area relative to total aortic luminal surface for LDL-R deficient mice treated according to Example 1.

According to a preferred process of the present invention, an aliquot of blood is extracted from a mammalian subject, preferably a human, and the aliquot of blood is treated ex vivo with certain stressors, described in more detail below. The terms "aliquot", "aliquot of blood" or similar terms used herein include whole blood, separated cellular fractions of the blood including platelets, separated non-cellular fractions of the blood including plasma, and combinations thereof. The effect of the stressors is to modify the blood, and/or the cellular or non-cellular fractions thereof, contained in the aliquot. The modified aliquot is then re-introduced into the subject's body by any method suitable for delivery, e.g., preferably selected from intra-arterial injection, intramuscular injection, intravenous injection, subcutaneous injection, intraperitoneal injection, and oral, nasal or rectal administration.

The stressors to which the aliquot of blood is subjected ex vivo according to the method of the present invention are selected from temperature stress (blood temperature above or below body temperature), an oxidative environment and an electromagnetic emission, in any combination, simultaneously or sequentially.

Preferably also, the aliquot of blood is in addition subjected to mechanical stress. Such mechanical stress is suitably that applied to the aliquot of blood by extraction of the blood aliquot through a conventional blood extraction needle, or a substantially equivalent mechanical stress, applied shortly before the other chosen stressors are applied to the blood aliquot. This mechanical stress may be supplemented by the mechanical stress exerted on the blood aliquot by bubbling gases through it, such as ozone/oxygen mixtures, as described below.

Suitably, in human subjects, the aliquot has a volume sufficient that, when re-introduced into the subject's body, at least partial alleviation of an endothelin-related disorder is achieved in the subject. Preferably, the volume of the aliquot is up to about 400 ml, preferably from about 0.1 to about 100 ml, more preferably from about 5 to about 15 ml, even more preferably from about 8 to about 12 ml, and most preferably about 10 ml. When a cellular fraction is used instead of whole blood, the aliquot should contain the number of blood cells which would ordinarily be contained in whole blood of the aforementioned volumes, e.g. $10^3$ to $10^{12}$.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and an electromagnetic emission, or an electromagnetic emission and oxidative stress. Care must be taken to utilize an appropriate level of the stressors to thereby effectively modify the blood to alleviate the endothelin-related disorder in the subject.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, alleviation of the disorder will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments, the aliquot is cooled below normal body temperature such that the mean temperature of the aliquot is within the range of from about −5° C. to about 36.5° C., even more preferably from about 10° C. to about 30° C., and even more preferably from about 15° C. to about 25° C.

The oxidative environment stressor can be the application to the aliquot of solid, liquid or gaseous oxidizing agents. Chemical oxidants such as hydrogen peroxide can be used. Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage such that the therapy is rendered ineffective. Suitably, the gas stream has an ozone content of up to about 300 μg/ml, preferably up to about 100 μg/ml, more preferably about 30 μg/ml, even more preferably up to about 20 μg/ml, particularly preferably from about 10 μg/ml to about 20 μg/ml, and most preferably about 14.5±1.0 μg/ml. The gas stream is suitably supplied to the aliquot at a rate of up to about 2.0 litres/min, preferably up to about 0.5 litres/min, more preferably up to about 0.4 litres/min, even more preferably up to about 0.33 litres/min, and most preferably about 0.24±0.024 litres/min. The lower limit of the flow rate of the gas stream is preferably not lower than 0.01 litres/min, more preferably not lower than 0.1 litres/min, and even more preferably not lower than 0.2 litres/min.

The electromagnetic emission stressor is suitably applied by irradiating the aliquot under treatment from a source of an electromagnetic emission while the aliquot is maintained at the aforementioned temperature and while the oxygen/ozone gaseous mixture is being bubbled through the aliquot. Preferred electromagnetic emissions are selected from photonic radiation, more preferably UV, visible and infrared light, and even more preferably UV light. The most preferred UV sources are UV lamps emitting primarily UV-C band wavelengths, i.e. at wavelengths shorter than about 280 nm. Such lamps may also emit amounts of visible and infrared light. Ultraviolet light corresponding to standard UV-A (wavelengths from about 315 to about 400 nm) and UV-B (wavelengths from about 280 to about 315) sources can also be used. For example, an appropriate dosage of such UV light, applied simultaneously with the aforementioned temperature and oxidative environment stressors, can be obtained from lamps with a combined power output of from about 45-65 mW/cm². Up to eight such lamps surrounding the sample bottle, with a combined output at 253.7 nm of 15-25 watts, operated at an intensity to deliver a total UV light energy at the surface of the blood of from about 0.025 to about 10 joules/cm$^2$, preferably from about 0.1 to about 3.0 joules/cm$^2$. Preferably, four such lamps are used.

The time for which the aliquot is subjected to the stressors is normally within the time range of up to about 60 minutes. The time depends to some extent upon the chosen intensity of the electromagnetic emission, the temperature, the concentration of the oxidizing agent and the rate at which it is supplied to the aliquot. Some experimentation to establish optimum times may be necessary on the part of the operator, once the other stressor levels have been set. Under most stressor conditions, preferred times will be in the approximate range of from about 2 to about 5 minutes, more preferably about 3 minutes. The starting blood temperature, and the rate at which it can be warmed or cooled to a predetermined temperature, tends to vary from subject to subject. Warming is suitably by use of one or more infrared lamps placed adjacent to the aliquot container. Other methods of warming can also be adopted.

As noted above, it is preferred to subject the aliquot of blood to a mechanical stressor, as well as the chosen stressor(s) discussed above. Extraction of the blood aliquot from the patient through an injection needle constitutes the most convenient way of obtaining the aliquot for further extracorporeal treatment, and this extraction procedure imparts a suitable mechanical stress to the blood aliquot. The mechanical stressor may be supplemented by subsequent processing, for example the additional mechanical shear stress caused by bubbling as the oxidative stressor is applied.

In the practice of the preferred process of the present invention, the blood aliquot may be treated with the stressors using an apparatus of the type described in U.S. Pat. No. 4,968,483 to Mueller, incorporated herein by reference. The aliquot is placed in a suitable, sterile, UV light-transmissive container, which is fitted into the machine. The UV lamps are switched on for a fixed period before the gas flow is applied to the aliquot providing the oxidative stress, to allow the output of the UV lamps to stabilize. The UV lamps are typically on while the temperature of the aliquot is adjusted to the predetermined value, e.g. 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

A subject preferably undergoes a course of treatments, each individual treatment comprising removal of a blood aliquot, treatment thereof as described above and re-administration of the treated aliquot to the subject. A course of such treatments may comprise daily administration of treated blood aliquots for a number of consecutive days, or may comprise a first course of daily treatments for a designated period of time, followed by an interval and then one or more additional courses of daily treatments.

In one preferred embodiment, the subject is given an initial course of treatments comprising the administration of 1 to 6, more preferably 4 to 6 aliquots of treated blood. In another preferred embodiment, the subject is given an initial course of therapy comprising administration of from 2 to 4 aliquots of treated blood, with the administration of any pair of consecutive aliquots being either on consecutive days, or being separated by a rest period of from 1 to 21 days on which no aliquots are administered to the patient, the rest period separating one selected pair of consecutive aliquots being from about 3 to 15 days. In a more specific, preferred embodiment, the dosage regimen of the initial course of treatments comprises a total of three aliquots, with the first and second aliquots being administered on consecutive days and a rest period of 11 days being provided between the administration of the second and third aliquots. For optimum effectiveness of the treatment, it is preferred that no more than one aliquot of modified blood be administered to the subject per day, in one or more injection sites, and that the maximum rest period between any two consecutive aliquots during the course of treatment be no greater than about 21 days.

It may be preferred to subsequently administer additional courses of treatments following the initial course of treatments. Preferably, subsequent courses of treatments are administered following a rest period of several weeks or months, preferably at least about three weeks, after the end of the initial course of treatments. In one particularly preferred embodiment, the subject receives a second course of treatments comprising the administration of one aliquot of treated blood every 30 days following the end of the initial course of treatments, for a period of 6 months. It may also be preferred in some circumstances to follow one or more of the above-described courses of treatment by periodic "booster" treatments, if necessary, to maintain the desired effects of the present invention. For example, it may be preferred to administer booster treatments at intervals of 3 to 4 months following the initial course of treatment.

It will be appreciated that the spacing between successive courses of treatments should be such that the positive effects of the treatment of the invention are maintained, and may be determined on the basis of the observed response of individual subjects.

The invention is further illustrated and described with reference to the following specific examples.

EXAMPLE 1

Model:

The purpose of the experiment is to determine the effects of treatment according the present invention on endothelin levels in the LDL receptor (LDL-R) deficient mouse model, a widely used transgenic atherosclerosis model created by targeted disruption of the LDL receptor.

The LDL-R deficient mouse model shows intolerance to cholesterol feeding and develops widespread atherosclerotic changes which progress to mature fibrous lesions morphologically indistinguishable from established human atherosclerosis. Apart from the defined genetic abnormality causing predisposition to atherosclerosis, this model has the advantage of rapid development of widespread atherosclerosis within 6 to 8 weeks following institution of cholesterol feeding.

Protocol:

LDL-R deficient mice in the C57BL/6J background were purchased from Jackson Laboratories. A total of 42 mice were entered into the study at 22 weeks of age. The length of the study was 8 weeks. The mice were maintained on a 12 hour dark/12 hour light cycle with unrestricted access to food and water.

The animals were randomly assigned to three experimental groups as follows: (I) control (12 animals, normal diet); (II) high cholesterol diet with injections of saline (15 animals); and (III) high cholesterol diet with administration of stressed blood according to the invention (15 animals).

No differences in food intake, drinking patterns, or body weight were noted between animals from each group. The high cholesterol diet contained 1.25% cholesterol, 7.5% (wt/wt) cocoa butter, 7.5% casein, and 0.5% (wt/wt) sodium cholate.

To ensure proper food intake, food consumption and animal weight were monitored on a weekly basis. In previous experiments, it was demonstrated that 8 weeks of feeding with the high cholesterol diet results in substantial atherosclerosis development, particularly in the aortic arch and the descending thoracic aorta.

Treatment:

The 15 animals of Group III underwent a course of treatment by a preferred method of the invention. The treatments began four weeks after initiation of the study, with each of the animals of Group III receiving a total of three treatments on days 29, 30 and 42 of the high cholesterol feeding.

The blood to be stressed was taken from syngeneic animals by cardiac puncture, pooled and anti-coagulated with sodium citrate (10 ml of blood and 2 ml of 3.13% sodium citrate solution). The blood aliquot (12 ml) was transferred to a sterile, disposable, low-density polyethylene vessel for ex vivo treatment, and was then treated simultaneously with a gaseous oxygen/ozone mixture and ultraviolet light at elevated temperature using an apparatus as generally described in aforementioned U.S. Pat. No. 4,968,483 to Mueller et al.

The constitution of the gas mixture was 14.5±1.0 μg ozone/ml, with the remainder of the mixture comprising medical grade oxygen. The gas mixture was bubbled through the aliquot at a rate of 240±24 ml/min for a period of 3 minutes. The temperature of the aliquot was held steady at 42.5±1.0° C. The UV light was within the UV-C band, and included a wavelength of 253.7 nm.

The treatment protocol consisted of administration, by intramuscular injection, of 30 μl of the treated syngeneic blood into each animal of Group III.

In the animals of Group II, 30 μl of saline blood was injected intramuscularly on days 29, 30 and 42 of high cholesterol feeding.

Assessment of Atherosclerosis:

After 8 weeks, the animals were anesthetized with zylaxine/ketamine and the heart was exposed. After nicking the vena cava to obtain blood samples, the animals were perfused via ventricular puncture, first with PBS to flush out the blood and then with 10% neutral buffered formalin for 3 minutes to fix the aorta. The thoracic aorta was dissected away from the thorax en bloc and stored in 10% formalin at 4EC. Pressure-fixed (10% formalin) aortae were removed en bloc and opened to allow a longitudinal full length inversion. The aortae were then mounted internally exposed on glass slides and stained with oil red O. The bright red staining (indicating lipid deposition) was then quantified using a computer assisted morphometric system, and expressed as a percentage of total aortic intimal surface.

Immunohisochemistry Studies

The aortae of 4 animals from each experimental group were divided into three regions: aortic arch, thoracic aorta and abdominal aorta. Paraffin sections (5 μm thickness) were cut from each region and endogenous peroxidase activity was quenched by 3% $H_2O_2$ in methanol for 20 minutes; nonspecific antibody binding was blocked with 10% goat serum in PBS for 30 minutes. Adjacent sections from each group of animals were immunostained using the following antibodies: (a) polyclonal rabbit ET-1 antibody (Peninsula Lab, Belmont, Calif.) at 1:200 dilution overnight at 4° C., and secondary reaction with goat anti-rabbit biotinylated antibody (1:250 dilution, Vector Laboratories, Burlingame, Calif.) for 45 min at room temperature; (b) polyclonal rat antibody to the mouse monocyte/macrophage marker MOMA-2 (Serotec Ltd., Oxford, United Kingdom) at 1:100 dilution overnight at 4° C., and secondary reaction with biotinylated rabbit anti-rat IgG (1:250 dilution, Vector Laboratories) for 45 minutes at room temperature; (c) monoclonal antibody to smooth muscle α-actin (Boehringer Manheim, Laval, Quebec) at 1:100 dilution for 60 minutes at room temperature and secondary reaction with biotinylated antimouse IgG (1:150 dilution, Vector Laboratories) for 30 minutes at room temperature. Following incubation with the secondary antibodies, the sections were treated with streptavidin-biotin-peroxidase complexes (Vectastain ABC kit, Vector Laboratories) for 30 minutes at room temperature. Diaminobenzadine was used as the peroxidase substrate and hematoxylin as the nuclear counterstain. Negative control slides were prepared by substituting preimmune rabbit serum for the primary antibody.

Statistical Analysis:

Statistical differences between groups were evaluated using the one-way ANOVA with post hoc student t-test where appropriate. Data are presented as mean ±SD.

Results:

Only minimal lipid deposition was found in the animals of Group I receiving normal mouse chow, while the animals of Group II which received the high cholesterol diet and the sham treatments exhibited substantial aortic lipid deposition, with involvement of more than 30% of the aorta. In contrast, the aortic lesions were significantly less in the treated animals of Group III ($p<0.05$), demonstrating that the treatment of the invention significantly reduced the extent of aortic atherosclerosis. FIG. 1 shows mean values for atherosclerotic area (n=8, group I; n=12, group II and n=11, group III). Asterisks indicate statistical difference versus group I using the one-way ANOVA test in conjunction with the Bonferroni correction (*$p<0.05$; **$p<0.001$). The cross sign indicated a statistical difference versus group II using the one-way ANOVA test ($p<0.01$).

In addition, the animals which were treated according to the preferred method of the present invention were observed to have better general appearance, reduced skin xanthomatosis (eyelids, nose and paws), reduced limb swelling, and better appetite than the untreated animals which received the high cholesterol diet.

Immunostaining with monoclonal antibody to smooth muscle α-actin revealed a similar pattern staining in both normal chow and high cholesterol fed animals, largely restricted to the medial layer of the vessels with only partial staining in the atherosclerotic lesion. In contrast, immunostaining with MOMA-2 showed a very dense accumulation of macrophages in the lesions of Group II animals, which was reduced with the treatment of the invention. Immunostaining for ET-1 on sequential sections revealed that expression of ET-1 was limited to endothelial cells and predominantly in the neointimal macrophage rich lesion of the atherosclerotic plaque of the high cholesterol fed animals. A negative control slide was prepared by substituting preimmune rabbit serum for the primary antibody. However, ET-1 staining was markedly reduced in the animals treated according to the invention.

The animals treated according to the method of the invention showed reduced atherosclerotic plaque formation, as well as reductions in area of macrophage and ET-1 staining. These results are consistent with a reduction in ET-1 production by the macrophages in the atherosclerotic plaque brought about by the method of the invention, which may be consistent with a decrease in chronic inflammation contributing to a reduction in progression of atherosclerosis in treated mice. Based on these results, it is expected that the method of the invention would be effective in the treatment of endothelin-related diseases, including those specifically mentioned above. Administration to patients susceptible to complication resulting from excess angiogenesis, e.g. patients recovering from cardiac events and liable to restenosis, is particularly indicated.

What is claimed is:

1. A method of alleviating the symptoms of, or treatment of, an primary pulmonary hypertension, in a patient in need thereof, which comprises:
   a) extracting an aliquot of blood from the patient, subjecting the aliquot extracorporeally to at least two stressors selected from the group consisting of a temperature above or below body temperature, ultraviolet light and ozone; and
   b) administering the aliquot of blood treated in step (a) to the patient, wherein the aliquot has a volume sufficient alleviate said primary pulmonary hypertension.

2. The method of claim 1 wherein all of the stressors are simultaneously administered to the aliquot.

3. The method of claim 2, wherein the ozone stressor comprises applying ozone to the aliquot.

4. The method of claim 3, wherein ozone applied to the aliquot is ozone gas, and the ozone gas is introduced into the blood aliquot in an amount which does not give rise to excessive levels of cell damage.

5. The method of claim 3, wherein the ozone applied to the aliquot comprises a mixture of ozone gas and medical grade oxygen, the ozone gas being contained in the mixture in a concentration of up to about 300 μg/ml.

6. The method of claim 5, wherein the ozone gas in the mixture is in a concentration of up to about 30 μg/ml.

7. The method of claim 5, wherein the ozone gas in the mixture is in a concentration of from about 13.5 μg/ml to about 15.5 μg/ml.

8. The method of claim 5, wherein the mixture is applied to the aliquot at a flow rate of up to about 0.33 litres/mm.

9. The method of claim 8, wherein the mixture is applied to the aliquot at a flow rate of from about 0.21 litres/mm to about 0.27 litres/mm.

10. The method of claim 2, wherein the ultra violet light stressor comprises ultraviolet light having one or more UV-C band wavelengths.

11. The method of claim 2, wherein the temperature stressor is applied so that the temperature of at least part of the aliquot is in the range of from about −5° C. to about 55° C.

12. The method of claim 2, wherein the mean temperature of the blood in the aliquot is in the range of from about 0° C. to about 36.5° C.

13. The method of claim 2, wherein the temperature is in the range of from about 37° C. to about 55° C.

14. The method of claim 13, wherein the temperature is 42.5±1° C.

15. The method of claim 2, wherein the volume of the aliquot is up to about 400 ml.

16. The method of claim 15, wherein the volume of the aliquot is about 10 ml.

17. The method of claim 2, wherein the aliquot is subjected to the stressors for a period of up to about 60 minutes.

18. The method of claim 17, wherein the aliquot is subjected to the stressors for a period of about 3 minutes.

19. The method of claim 2, wherein the blood is administered to the mammal by a method suitable for delivery selected from the group consisting of intra-arterial injection, intramuscular injection, intravenous injection, subcutaneous injection, intraperitoneal injection, and oral, nasal or rectal administration.

* * * * *

UNITED STATES PATENT AND TRADEMARK OFFICE
CERTIFICATE OF CORRECTION

| | | |
|---|---|---|
| PATENT NO. | : 7,255,880 B2 | Page 1 of 1 |
| APPLICATION NO. | : 10/815509 | |
| DATED | : August 14, 2007 | |
| INVENTOR(S) | : Anthony E. Bolton, Arkady Mandel and Duncan J. Stewart | |

It is certified that error appears in the above-identified patent and that said Letters Patent is hereby corrected as shown below:

Claim 8, Column 10, line 5, please replace "0.33 litres/mm." with --0.33 litres/min.--

Claim 9, Column 10, line 7, please replace "0.21 litres/mm" with --0.21 litres/min--

Claim 9, Column 10, line 8, please replace "0.27 litres/mm" with --0.27 litres/min.--

Signed and Sealed this

Twenty-seventh Day of November, 2007

JON W. DUDAS
*Director of the United States Patent and Trademark Office*